US007981426B2

(12) United States Patent
Kim

(10) Patent No.: US 7,981,426 B2
(45) Date of Patent: *Jul. 19, 2011

(54) METHOD FOR STIMULATING WOUND HEALING

(75) Inventor: Sunghoon Kim, Seoul (KR)

(73) Assignee: aTyr Pharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,714

(22) Filed: Aug. 10, 2009

(65) Prior Publication Data

US 2010/0041608 A1     Feb. 18, 2010

Related U.S. Application Data

(63) Continuation of application No. 11/829,018, filed on Jul. 26, 2007, now Pat. No. 7,572,452, which is a continuation of application No. 10/623,567, filed on Jul. 22, 2003, now Pat. No. 7,282,208.

(30) Foreign Application Priority Data

Jul. 22, 2002   (KR) ........................ 10-2002-0042858

(51) Int. Cl.
    *A61K 38/17*     (2006.01)
    *A61K 38/18*     (2006.01)
    *C07K 14/435*    (2006.01)
    *C07K 14/475*    (2006.01)

(52) U.S. Cl. .................. 424/185.1; 424/198.1; 514/9.4; 530/350; 530/399

(58) Field of Classification Search ........................ None
See application file for complete search history.

(56) References Cited

U.S. PATENT DOCUMENTS

| 6,875,749 | B2 | 4/2005 | Schwarz et al. | 514/44 |
| 6,916,648 | B2 | 7/2005 | Goddard et al. | 435/252.3 |
| 7,282,208 | B2 * | 10/2007 | Kim | 424/185.1 |
| 7,572,452 | B2 * | 8/2009 | Kim | 424/185.1 |
| 2002/0160957 | A1 * | 10/2002 | Stern et al. | 514/13 |

FOREIGN PATENT DOCUMENTS

WO     WO 01/95927 A1    12/2001

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Park et al. Monocyte cell adhesion induced by a human aminoacyl-tRNA synthetae-associated factor, p43: identification of the related adhesion molecules and signaling pathways. J Leuk Biol 71: 223-230, 2002.*
Park et al. The novel cytokine p43 stimulates dermal fibroblast proliferation and wound repair. Am J Pathol 166(2): 387-398, 2005.*
Kao et al. Characerization of a novel tumor-derived cytokine. J Biol Chem 269(40): 25106-25119, 1994.*
Ko et al. A cofactor of tRNA synthetase, p43, is secreted to up-regulate proinflammatory genes. J Biol Chem 276(25): 23028-23033, 2001.*
Ben-Izhak et al., "Ki67 antigen and PCNA proliferation markers predict survival in anorectal malignant melanoma," *Histopathology* 41:519-525, 2002.
Bennett et al., "Growth Factors and Wound Healing: Biochemical Properties of Growth Factors and Their Receptors," *Am. J. Surgery* 165:728-737, Jun. 1993.
Berger et al., "Endothelial Monocyte-Activating Polypeptide II, a Tumor-Derived Cytokine That Plays an Important Role in Inflammation, Apoptosis, and Angiogenesis," *J. Immunotherapy* 23(5):519-527, 2000.
Cecconi et al., "Gene-trap: a way to identify novel genes and unravel their biological function," *FEBS Letters* 480:63-71, 2000.
Chang et al., "Interaction of the C-terminal Domain of p43 and the α Subunit of ATP Synthase," *J. Biol. Chem.* 277(10):8388-8394, Mar. 8, 2002.
Gallucci et al., "Impaired cutaneous wound healing in interleukin-6-deficient and immunosuppressed mice," *The FASEB J.* 14:2525-2531, Dec. 2000.
Knighton et al., "Regulation of Cutaneous Wound Healing by Growth Factors and the Microenvironment," *Invest. Radiol.* 26:604-611, Jun. 1991.
Ko et al., "Biphasic regulation of angiogenesis by a cofactor of aminoacyl-tRNA synthetase, p43," *Molecular Biol. Of the Cell* 12:127a, Nov. 2001.
Lund et al., "Functional overlap between two classes of matrix-degrading proteases in wound healing," *The EMBO Journal* 18(17):4645-4656, 1999.

(Continued)

*Primary Examiner* — Bridget E Bunner
(74) *Attorney, Agent, or Firm* — Seed IP Law Group PLLC

(57) ABSTRACT

The present invention relates to a method for stimulating wound healing, and more particularly to a method for stimulating wound healing in a subject in need thereof, comprising administering to a wound of the subject an effective amount for stimulating wound healing of a composition, wherein the composition comprises p43 having an amino acid sequence set forth in SEQ ID NO: 1 or functional equivalents thereof. The composition used in the method of the present invention can be efficiently utilized for the wound healing, since p43, an effective ingredient of the composition, has an excellent effect on the wound healing by its action including the induction of macrophage/monocyte and endothelial cell re-epithelization, proliferation of fibroblasts or angiogenesis.

10 Claims, 11 Drawing Sheets

OTHER PUBLICATIONS

Park et al., "Dose-dependent Biphasic Activity of tRNA Synthetase-associating Factor, p43, in Angiogenesis," *J. Biol. Chem.* 277(47):45243-25248, Nov. 22, 2002.

Park et al., "Precursor of Pro-apoptotic Cytokine Modulates Aminoacylation Activity of tRNA Synthetase," *J. Biol. Chem.* 274(24):16673-16676, Jun. 11, 1999.

Southern, "Detection of Specific Sequences Among DNA Fragments Separated by Gel Electrophoresis," *J. Mol. Biol.* 98:503-517, 1975.

Steed, "Modifying the Wound Healing Response With Exogenous Growth Factors," *Clinics in Plastic Surgery* 25(3):397-405, Jul. 1998.

Werner et al., "The Function of KGF in Morphogenesis of Epithelium and Reepithelialization of Wounds," *Science* 266:819-822, Nov. 4, 1994.

Zambrowicz et al., "Disruption and sequence identification of 2,000 genes in mouse embryonic stem cells," *Nature 392*:608-611, Apr. 9, 1998.

Ziak et al., "Two Isoforms of Trimming Glucoside II Exist in Exist in Mammalian Tissues and Cell Lines but Not in Yeast and Insect Cells," *Biochem. And Biophys. Res. Comm.* 280(1):363-367, 2001.

\* cited by examiner

SEQUENCE LISTING

```
<160> NUMBER OF SEQ ID NOS: 7

<210> SEQ ID NO 1
<211> LENGTH: 312
<212> TYPE: PRT
<213> ORGANISM: Homo sapiens

<400> SEQUENCE: 1

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80
```

```
Pro Ser Gly Thr Pro Leu His Ala Asn Ser Met Val Ser Glu Asn Val
            85                  90                  95

Ile Gln Ser Thr Ala Val Thr Val Ser Ser Gly Thr Lys Glu Gln
        100                 105                 110

Ile Lys Gly Gly Thr Gly Asp Glu Lys Ala Lys Glu Lys Ile Glu
        115                 120                 125

Lys Lys Gly Glu Lys Lys Glu Lys Lys Gln Gln Ser Ile Ala Gly Ser
        130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
        210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Val Cys Arg Ala Gln
        290                 295                 300

Thr Met Ser Asn Ser Gly Ile Lys
305                 310

<210> SEQ ID NO 2
<211> LENGTH: 108
<212> TYPE: DNA
<213> ORGANISM: Artificial Sequence
<220> FEATURE:
<223> OTHER INFORMATION: Probe for Southern Blot

<400> SEQUENCE: 2
tgaatgaact gcaggacgag gcagcgcggc tatggtggct ggccacgacg ggcgttcctt      60
gcgcagctgt gctcgacgtt gtcactgaag cgggaaggac tggctgct                 108

<210> SEQ ID NO 3
<211> LENGTH: 1226
<212> TYPE: DNA
<213> ORGANISM: Artificial Sequence
<220> FEATURE:
<223> OTHER INFORMATION: Probe for Southern Blot
<220> FEATURE:
<221> NAME/KEY: misc_feature
<222> LOCATION: 53, 54, 55, 56, 57, 58, 59, 60, 61, 62, 63, 64, 65, 66,
      67, 68, 69, 70,71,72, 73, 74, 75, 76, 77, 78, 79, 646,647,
      648,649
<223> OTHER INFORMATION: n = A,T,C or G
<220> FEATURE:
<221> NAME/KEY: misc_feature
<222> LOCATION: 650,651,652,653,654,655,656,657,658,659,660,661,662,663,
      1212,1213,1214,1215,1216,1217,1218,1219,1220,1221
<223> OTHER INFORMATION: n = A,T,C or G

<400> SEQUENCE: 3
```

```
aagcttcgac catatgggag agctcccaac gcgttggatg catagcttga gtnnnnnnnn      60
nnnnnnnnnn nnnnnnnnng aattcaataa ggagactttt taaaaagata tttttatctt     120
aatgtgtgtg tgcctgcatt tgtgtgtatg caccattgcg tgcataccta gagcctgcag     180
aggctagaag aggggttcaa cctggaactg aggctacagg tggttgttga gtatccacat     240
agatgctcgg aattaaacct gggttctcca gtcccaagga gactaaatat tttcaaagta     300
agcctgcact ttgtactaca gtaaaataaa accactgtgg agtgactaat ataaaatagt     360
aagatgagct ctagattaac aggcaaaagt ttaagttttc agtattgtta aagtagcacc     420
atctccctaa agagaaccat atttattttc cttccagtct tctgtgtttc cctcttttgt     480
ttgaaagttt agtgagtgct tattttctct actgtgaaca caacatgaga caaactcagg     540
gattgtaaga gatcatggac ataaattact tttaggaacc tggcactcaa atgaaaatta     600
attagtgaca agttggcatg gcattttatt attaaccctg ggtggnnnnn nnnnnnnnnn     660
nnntaaactg cgtggtgatg atttgtgatt gcaagaagac atagatatga agctctgaac     720
aacagtgtcc aggcaacatg tgaagaaaag gccctatgga ggggcaggag agcaggtgag     780
agcatcctaa tagaaattca gacagtgaag caagaagttg ttcacacagc ccacacagcc     840
tgttaagtgt tcttcactta aggtttgttg actgtaacca ccttttctaa agaaaacatt     900
aagaaaaaca taggtgtctg ttcgcttcct atttgctgct gtgattaaaa cgctgaccaa     960
aagcaacttg gctgaggagc cgttttttgta tttctccgtt taggtagcaa tgaagttgga    1020
gcaggaggaa gggtgcttac aggctagctc tcctgctctc cttgagcaag cattcttgtg    1080
gtagctcagg actccctgca cagtgacaca ccacgtgctt cttcagggggg acttcaaact   1140 actgtacacc ctttccttct gtcgaccata tgggagagct cccaacgcgt tggatgcata    1200
gcttgagtat tnnnnnnnnn nagctt                                         1226
```

<210> SEQ ID NO 4
<211> LENGTH: 30
<212> TYPE: DNA
<213> ORGANISM: Artificial Sequence
<220> FEATURE:
<223> OTHER INFORMATION: IF3 primer for PCR

<400> SEQUENCE: 4

```
gaggacaatg tgctccataa acactcactg                                       30
```

<210> SEQ ID NO 5
<211> LENGTH: 27
<212> TYPE: DNA
<213> ORGANISM: Artificial Sequence
<220> FEATURE:
<223> OTHER INFORMATION: IF3 primer for PCR

<400> SEQUENCE: 5

```
cgttacttaa gctagcttgc cacctac                                          27
```

<210> SEQ ID NO 6
<211> LENGTH: 31
<212> TYPE: DNA
<213> ORGANISM: Artificial Sequence
<220> FEATURE:
<223> OTHER INFORMATION: pKOF2 primer for PCR

<400> SEQUENCE: 6

```
tgacatggtt gccagagaag gttctcaagg a                                     31
```

<210> SEQ ID NO 7

-continued

```
<211> LENGTH: 838
<212> TYPE: DNA
<213> ORGANISM: Artificial Sequence
<220> FEATURE:
<223> OTHER INFORMATION: p43-specific probe for Northern Blot

<400> SEQUENCE: 7
ggtcaccgct tcatgtttct ctgccgattc tggggaaaga tggcaacgaa tgatgctgtt      60
ctgaagaggc tggagcagaa gggtgcagag gcggatcaga tcatcgaata tctcaagcag     120
caggttgctc ttcttaagga gaaagcaatt ttgcaggcaa caatgagaga agaaaagaaa     180
cttcgagttg aaaatgctaa actgaaaaaa gaaatagaag agctaaagca agagctgatt     240
ctggcagaaa ttcataacgg agtggagcaa gtgcgtgttc gattgagtac tccactgcag     300
acgaactgta ctgcttctga aagtgtggtg cagtctccat cagtagcaac caccgcctct     360
cctgctacaa aagagcagat caaagcggga gaagaaaaga aggtgaaaga gaagactgaa     420
aagaaaggag agaaaaagga gaagcagcag tcggcagcag caagtactga ctccaagcct     480
atcgacgcat cgcgtctgga tcttcgaatt ggttgtattg ttactgccaa gaagcaccct     540
gatgcagatt cactgtatgt ggaggaagta gatgtgggag aagcagcccc gcgcacggtc     600
gtcagcgggc tggtgaatca tgttcctcta gaacagatgc aaaatcgtat ggtggtttta     660
ctctgtaatc tgaagcctgc aaagatgcgg ggagttctgt ctcaagccat ggtgatgtgt     720
gccagttcac cagagaaagt ggagattctg gcccctccca acgggtccgt tcctggggac     780
agaattactt ttgatgcttt tcctggagag cctgacaagg agctaaaccc taagaaga     838
```

METHOD FOR STIMULATING WOUND HEALING

CROSS-REFERENCES TO RELATED APPLICATIONS

This application is a continuation of U.S. Application No. 11/829,018 filed Jul. 26, 2007, now U.S. Pat. No. 7,572,452 issued Aug. 11, 2009; which application is a continuation of U.S. application Ser. No. 10/623,567 filed Jul. 22, 2003, now U.S. Pat. No. 7,282,208 issued Oct. 16, 2007; which claims the benefit of Korean Patent application Ser. No. 10-2002-42858, filed Jul. 22, 2002, all of which are herein incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120161_402C2_SEQUENCE_LISTING.txt. The text file is 7 KB, was created on Aug. 10, 2009, and is being submitted electronically via EFS-Web, concurrent with the filing of the specification.

FIELD OF THE INVENTION

The present invention relates to a method for stimulating wound healing, and more particularly to a method for stimulating wound healing in a subject in need thereof, comprising: administering to a wound of the subject an effective amount for stimulating wound healing of a composition, wherein the composition comprising p43 having an amino acid sequence set forth in SEQ ID NO: 1 or functional equivalents thereof.

BACKGROUND OF THE INVENTION

In general, wound healing is any reaction of tissue against damage inflicted upon the tissue, and it is known as a complex biological process comprising chemotaxis, cell differentiation and replication, synthesis of matrix protein, angiogenesis and reconstitution of wound, as a series of tissue repair processes (Steed, D. L. et al., *Clin. Plast. Surg.* 25:397, 1998). As one of the typical factors for controlling wound healing process, the growth factor may be considered, which regulate cell growth, cell differentiation, cell metabolism and the like through the general wound healing process, as well as the environment around a wound, and have consistently been used for the development of treatment agents. In addition, various kinds of cytokine are known to participate in wound healing. As an example of the cytokine, there is transforming growth factor-β (TGF-β). The TGF-β is involved in the growth and differentiation of various cells. It has been reported that the TGF-β is involved in several complicated functions including growth control, the regulation of immune response, the stimulation of osteogenesis, the induction of cartilage-specific macromolecule and the promotion of wound healing (Bennett, N. T. et al., *Am. J. Surg.* 165:728, 1993).

According to whether skin deficiency exists or not, a wound may be classified into two types and may be treated with different healing mechanisms. When a wound does not involve skin deficiency, as in most mild injuries, for example a case of having injury only to the epidermis, keratinocytes move from the wound periphery, cover the wound, and reform new epidermis and keratin (Knighton, D. R. and Fiegel, V. D., *Invest. Radiol.* 26:604-611, 1991). However, when entire skin layers are totally injured or destroyed, new connective tissues, called granulation tissues, fill wound space where regenerated epidermis from the periphery of the wound sites must be covered. The granulation tissues are formed by the deposition of extracellular matrix components, such as collagen, from fibroblasts moving into the wound space. Consequently, the healing mechanisms of wound significantly varied depending on the presence of such skin deficiency. Successful wound healing requires completing a series of wound healing multistage processes. Since the deletion of one or more of wound healing-related components prevents the wound healing and skin repair, the wound remains exposed. Such an exposed wound can be easily infected, resulting in delayed healing processes, and the formation of ulcers and erosion of skin. There is a need for the development of a drug promoting the growth of granulation tissue and the regeneration of skin on wound involving skin deficiency.

Meanwhile, p43 is a protein consisting of 312 amino acids which is associated with a multi-tRNA synthetase complex to facilitate the catalytic activity of the bound enzyme. The p43 is highly expressed by microneuron in the lesions of autoimmune diseases in vitro including encephalomyelitis, neuritis and uveitis. The phenomenon in which p43 is highly expressed at certain developmental stages and tissues suggests that p43 is related to inflammation response and cell apoptosis (Berger, A. C. et al., *J. Immunother.* 23:519-527, 2000). We have previously shown that p43 can be employed as an effective cytokine and an anti-tumor agent (PCT International application No. PCT/KR00/00630). However, it is still not shown that p43 may be employed for treating wound. We identified that p43 has a novel activity of promoting wound healing process by acting on the wound healing process comprising the inflammation stage, epithelization stage and angiogenesis stage, and completed the present invention.

SUMMARY OF THE INVENTION

Therefore, it is an object of the present invention to provide a method for stimulating wound healing in a subject in need thereof, comprising administering to a wound of the subject an effective amount for stimulating wound healing of a composition, wherein the composition comprises p43 having an amino acid sequence set forth in SEQ ID NO: 1 or functional equivalents thereof.

BRIEF DESCRIPTION OF THE DRAWINGS

The foregoing and other objects, features and advantages of the present invention will become more apparent from the following detailed description when taken in conjunction with the accompanying drawings in which.

Ho: homozygous mutant mouse;

WT: wild type mouse which is not treated with p43 (control);

WT+p43: wild type mouse treated with p43.

Figure 5:
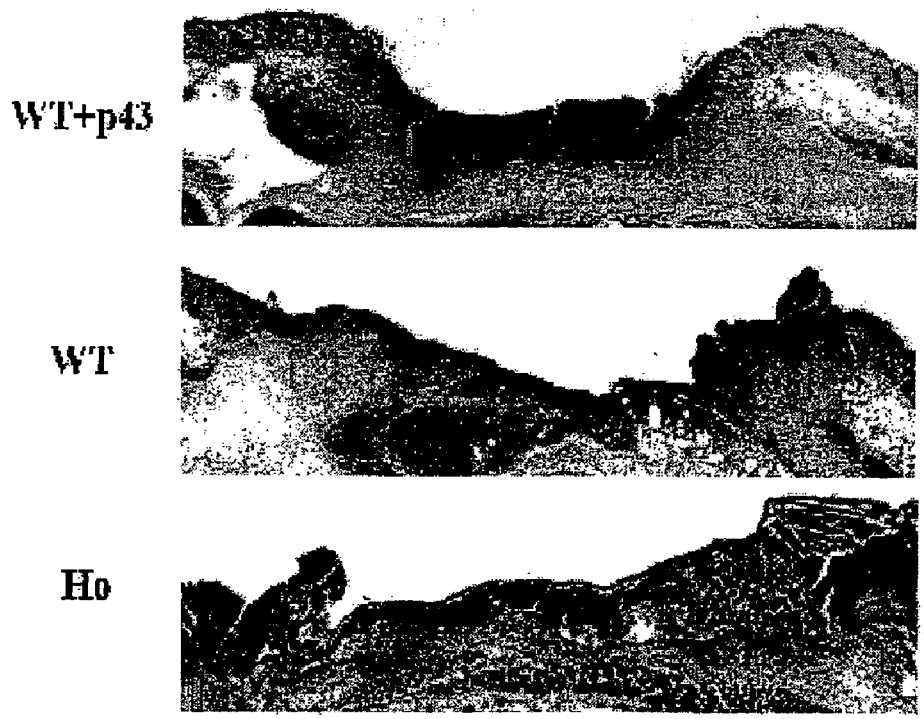

FIG. 5 shows the result of histochemical analysis representing the effect of p43 to stimulate wound healing.

Arrows: advancing epithelial layers;

Purple region: granulation tissues.

Figure 6:
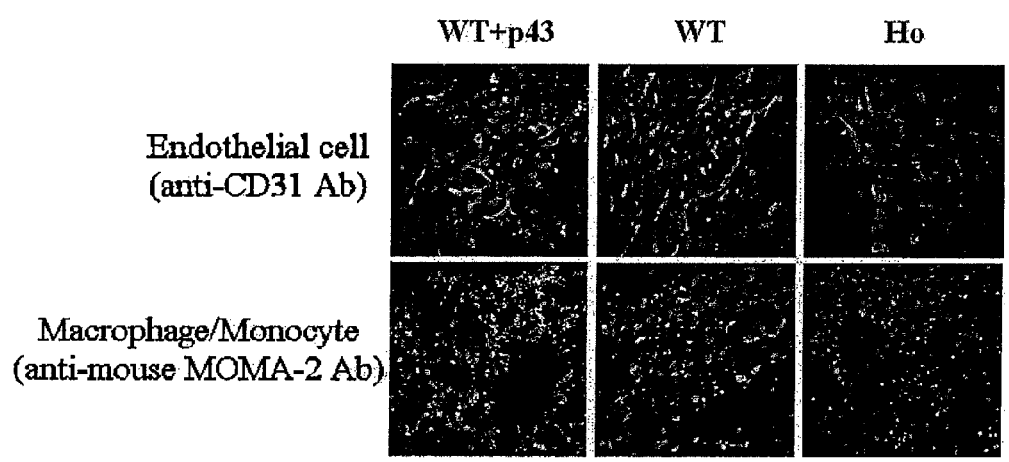

FIG. 6 shows the results of immunostaining for determining the generation levels of macrophage/monocyte and endothelial cells.

Figure 7:
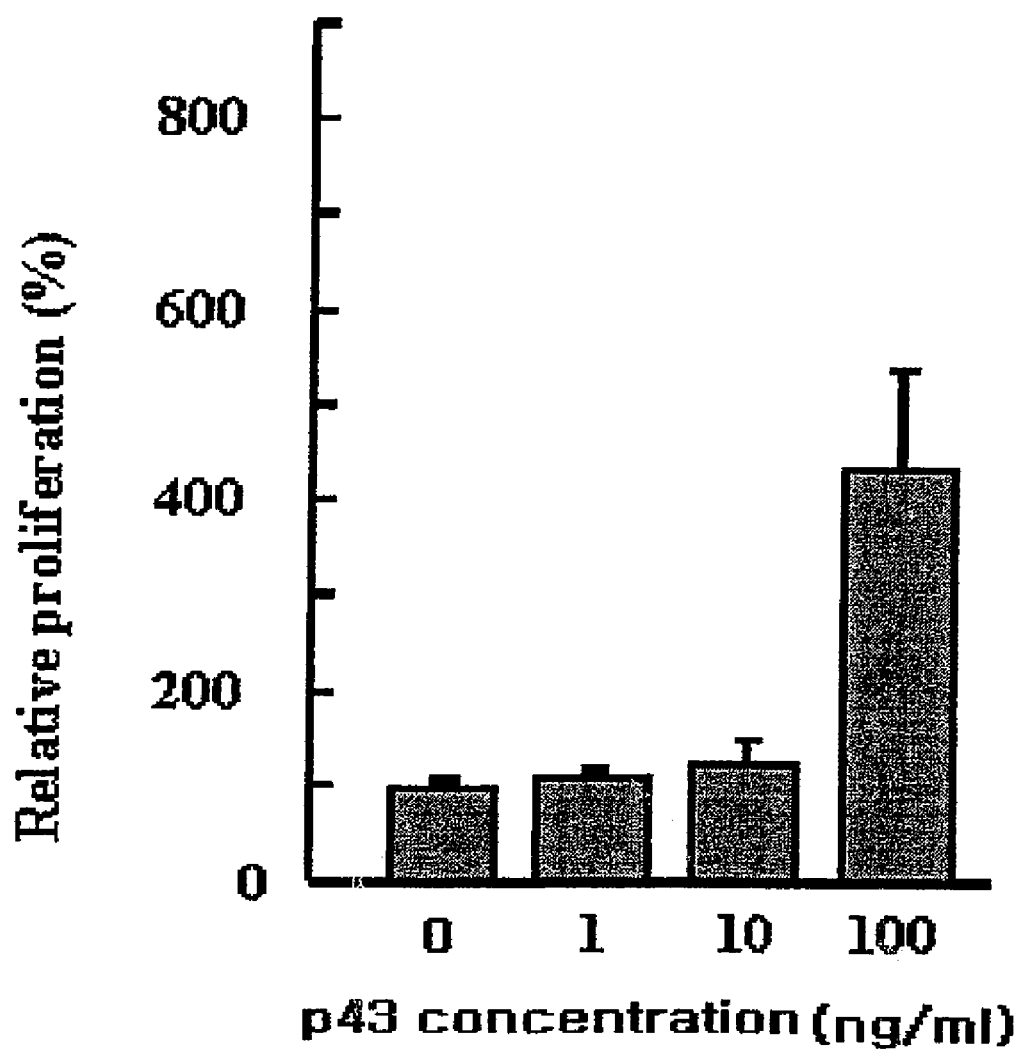

FIG. 7 is a bar graph representing the effect of p43 on the proliferation of fibroblasts.

Figure 8:

FIG. 8 shows the result of histochemical analysis representing the effect of p43 on the proliferation of fibroblasts.

Left: hematoxylin and eosin staining result of the crosssection of the wound area (arrows: the boundary of the wound area);

Right: immuno-fluorescence staining results of the boxed region in the wound area with the antibody against Ki-67.

Figure 9:
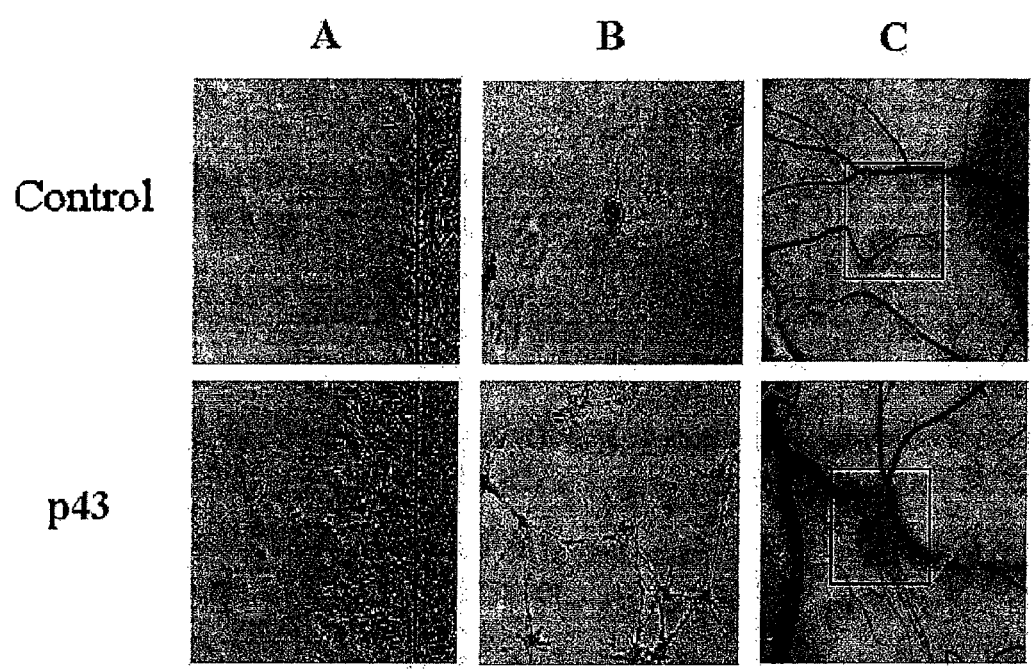

FIG. 9 shows the results of wound migration assay (A), tube formation assay (B) and CAM assay (C) for estimating the effect of p43 in blood vessel generation.

Figure 10:
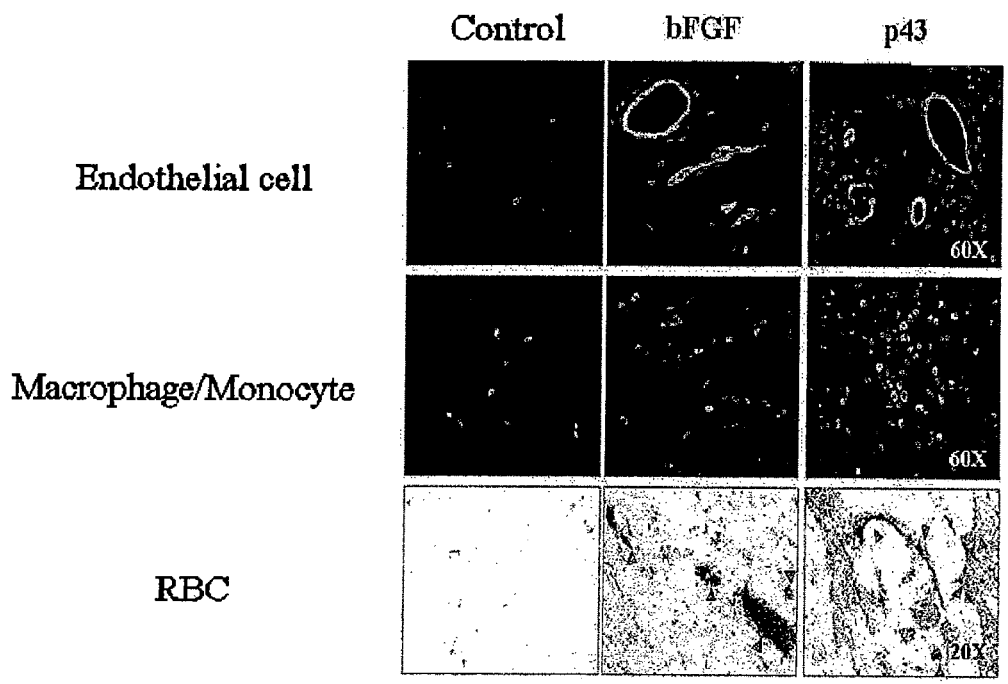

FIG. 10 shows the results of the matrigel plug assay for confirming the stimulation of neovascularization by p43.

Figure 11:
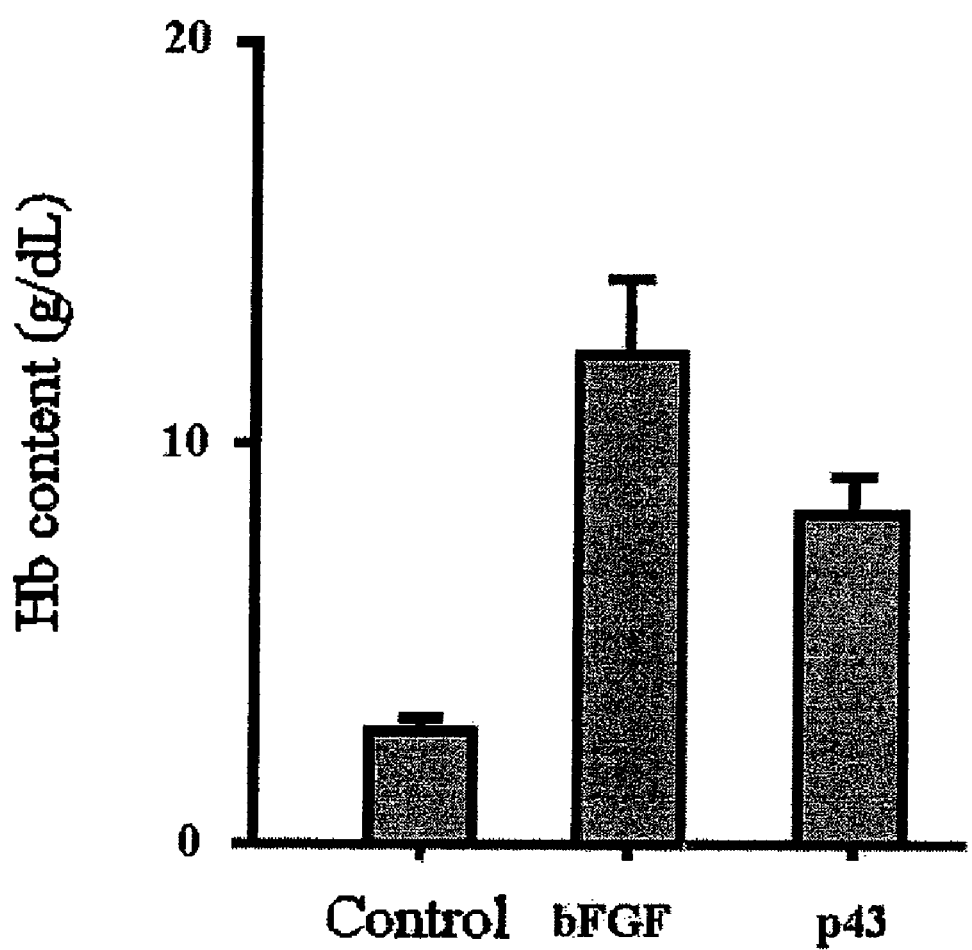

FIG. 11 is a bar graph representing the hemoglobin (Hb) contents within matrigel containing p43.

DETAILED DESCRIPTION OF THE INVENTION

According to an aspect of the present invention, there is provided a method for stimulating wound healing in a subject in need thereof, comprising administering to a wound of the subject an amount of a composition effective for stimulating wound healing, wherein the composition comprises a polypeptide selected from the group consisting of:

(a) a polypeptide having an amino acid sequence set forth in SEQ ID NO: 1; and (b) a polypeptide having at least 70% sequence homology with the polypeptide of (a).

Hereinafter, the term "wound" includes any injury to any portion of the body of a subject including, but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, incisions, excoriations, those injuries sustained in automobile and other mechanical accidents, and those caused by bullets, knives and other weapons, ulcer such as pressure ulcer, plaster ulcer and decubitus ulcer, and post-surgical injuries, as well as chronic conditions such as pressure sores, bedsores, conditions related to diabetes and poor circulation, and all types of acne. In addition, said wound includes dermatitis such as impetigo, intertrigo, folliculitis and eczema.

Areas of the body which can be treated with the present invention include, but are not limited to, skin, muscle and internal organs. Hereinafter, the term "subject" refers to a human or lower animal on whom the present invention is practiced.

The composition used in the present invention comprises, as an effective ingredient, p43 having an amino acid sequence set forth in SEQ ID NO: 1. The composition used in the present invention may also comprise the functional equivalents of the p43 as well as the p43. "Functional equivalents", as used herein, refer to polypeptides having the physiological activity to stimulate wound healing substantially equivalent with that of p43 having the amino acid sequences set forth in SEQ ID NO: 1. The functional equivalents may be a polypeptide having at least 70% sequence homology, preferably at least 80%, more preferably at least 90%, and most preferably at least 95%, compared to the amino acid sequence set forth in SEQ ID NO: 1. The functional equivalents include amino acid sequence variants, for example, in which a portion or all of natural p43 amino acid sequence is substituted, or a portion of the p43 amino acid sequence is deleted or added. The substitution of the amino acid is preferably a conservative substitution. For example, the amino acids occurring the conservative substitution in nature include aliphatic amino acids (Gly, Ala, Pro); hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). The amino acid deletion is preferably located at a portion that does not affect the physiological activity of p43.

Herein, p43 or functional equivalents thereof can be administered (or applied) in an appropriate amount depending on the size of wound. In the case of a circular excision wound of bilateral symmetry having a diameter of 0.5 cm, the p43 is preferably administered in a amount range of about 1 ng to 5 µg.

The composition comprising, as an effective component, the p43 or functional equivalents thereof according to the present invention may further comprise at least one selected from the group consisting of antibiotics, such as tetracycline, oxytetracycline, gentamicin, neomycin sulfate, bacitracin and polymyxin B sulfate; antihistamines, such as diphenhydramine, promethazine, tripelennamine, phenothiazine, chlorophenylamine, antazoline and pantholin; anti-inflammatory drugs; anti-viral drugs; anti-fungal agents; and growth factors, such as PDGF (platelet-derived growth factor), PDAF, PDEGF, TGF-β (transforming growth factor-β), PF-4, a FGF, bFGF (basic fibroblast growth factor), VEGF (vascular endothelial growth factor), GH (growth hormone), EGF (epidermal growth factor) and IGF (insulin-like growth factor).

The composition used in the present invention may be compounded with a pharmaceutically acceptable carrier and employed in the form of powder, liniment, gel, lotion, cream, ointment, paste, puff, aerosol or suppository, and in particular, ointment and paste are more preferable. The carrier may comprise hydrocarbons including petrolatum, liquid paraffin and gelling hydrocarbon; animal or vegetable oils including medium chain triglyceride, pig fat, hard fat and cacao oil; higher fatty alcohols including cetanol and stearyl alcohol; fatty acids and esters thereof including stearic acid isopropyl palmitate; aqueous bases including polyethylene glycol, 1,3-butyleneglycol, glycerol, gelatin, white sugar and sugar alcohol;

emulsifiers including glycerine fatty acid esters, polyoxyl stearate and polyoxyethylene hydrogenated castor oil; conglutinants including acrylate ester and sodium alginate; propellants including liquefied petroleum gas and carbon dioxide; and preservatives including paraoxybenzoates, depending on each formulation type.

When damaged skin was exposed to exterior environment, the damaged region may be infiltrated by toxins or bacteria, resulting in inflammation due to body's defense function. In treatment, the rapid generation of granulation tissue should be fostered in the damaged region and, above all, it is important for bacterial infection or excessive inflammation to be suppressed. Otherwise, not only much time is necessary in wound healing but also big scars will remain. The p43 having an amino acid sequence set forth in SEQ ID NO: 1 shows excellent effects on rapid healing of a wound by increasing granulation tissue and stimulating angiogenesis (blood vessel generation) in any wound including scald and ulcer regions.

The stimulation of wound healing by p43 identified in the present invention is considered to be a result from its multiple effect on inflammation as well as angiogenesis. The attraction of macrophage/monocyte by p43 is consistent with our expectation because various proinflammatory cytokines and chemokines such as monocyte chemotactic protein 1 (MCP-1) or macrophage inflammatory protein 1α (MIP-1α) have been reported to be induced by p43 [Young-Gyu Ko, et al., *J. Biol. Chem.* 276:23028-23033, 2001]. However, the pro-angiogenic activity of p43 shown in the present invention is surprising because p43 was previously shown to suppress the cell proliferation and induce apoptosis of endothelial cells at high concentration [Sun Young Chang, et al., *J. Biol. Chem.*, 277:8388-8394, 2002]. Based on these results, the present invention provides the first evidences on a novel activity of p43 in angiogenesis associated with wound repair.

As can be seen from the foregoing, p43, an effective ingredient of the composition of the present invention has a novel physiological activity including the induction of macrophage/monocyte and endothelial cell, re-epithelization, proliferation of fibroblasts or angiogenesis. Therefore, it is expected that the method for stimulating wound healing using the composition containing the p43 or functional equivalents thereof according to the present invention can be extensively used in the general medical areas involving wound healing.

Figure 1:
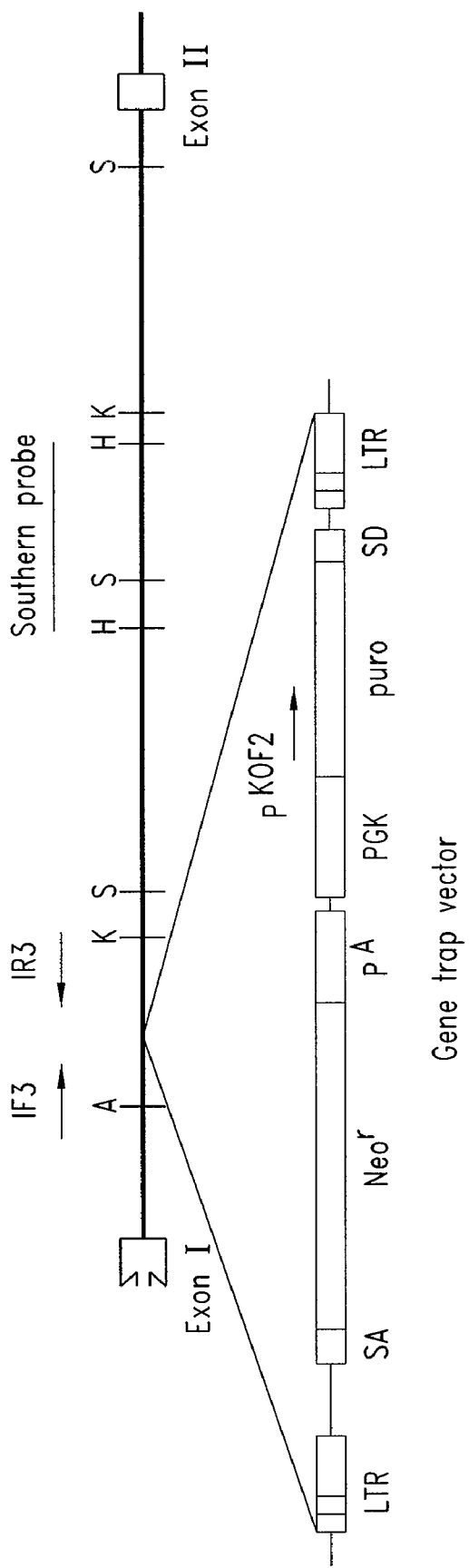
FIG. 1 is a schematic drawing showing where the gene trap is inserted within p43 mutant allele, wherein A, K, S and H indicate the restriction sites for Apa I, Kpn I, Sac I and HindIII, respectively. IF3, IR3 and pKOF2 are primers for PCR.

In a preferred embodiment of the present invention, the present inventors introduced a mutation to the structural gene of p43 in mouse. The mutation of the mouse genomic DNA may be effected according to conventional methods used in the prior art, including a gene trap method, a gene targeting method or an N-ethyl-N-nitrosourea (ENU) treatment method. Specifically, the gene trap vector was used herein to mutate the mouse genomic DNA. The gene trap vector may be one of those conventionally used in the prior art. More preferably, the gene trap vector may be VICTR20 vector. The VICTR20 comprises two functional units, a neomycin resistant gene (β-geo/neo$^r$) and a puromycin resistant gene (puro) (see FIG. 1). The neomycin resistant gene is expressed by an upstream promoter of genomic DNA in which the vector is inserted and the puromycin resistant gene is expressed by the phosphoglycerate kinase-1 (PGK) promoter of the vector. As shown in FIG. 1, the gene trap vector, VICTR20 includes long terminal repeats (LTRs) in both ends, a splice accepter (SA), a neomycin resistant gene (neo$^r$), a poly-A sequence (pA), a PGK promoter, a puromycin resistant gene (puro) and a splice donor (SD).

Then, to construct a mutant library, the genomic DNA in which a mutation is derived from the insertion of the gene trap is introduced into embryonic stem cells of mice. In the mutant library, the clone containing the disrupted p43 gene is identified and used to prepare heterozygous mutant mice.

Figure 2:
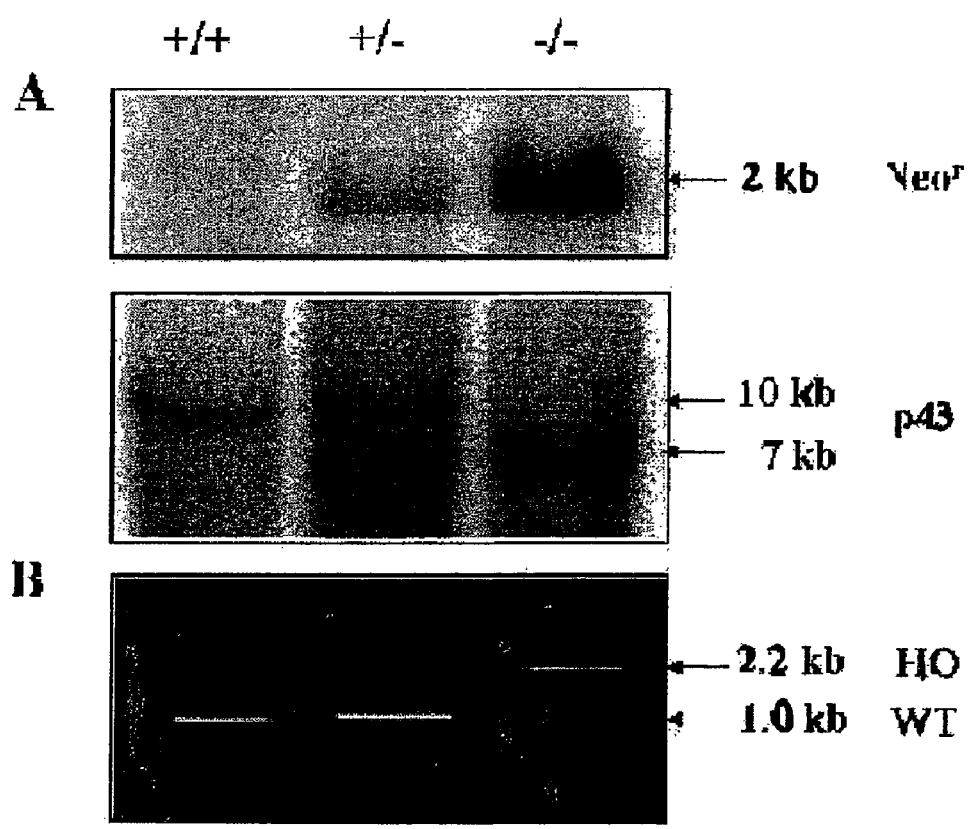
FIG. 2 shows the results of Southern blot (A) and PCR (B) for identifying the mutation of p43.
+/+: wild type mouse (WT);
+/−: heterozygous mutant mouse;
−/−: homozygous mutant mouse (Ho).
Figure 3:
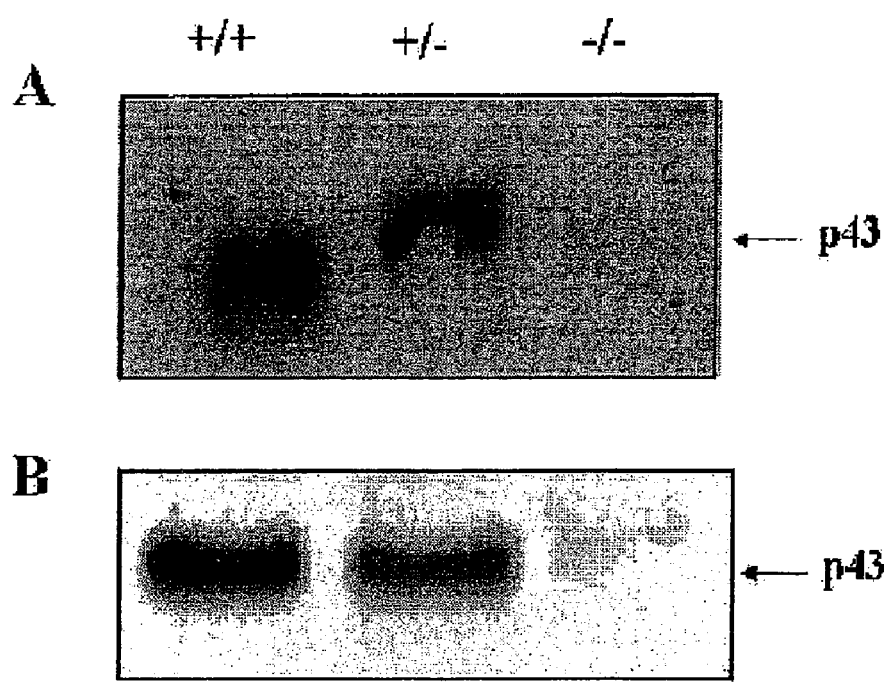
FIG. 3 shows the results of Northern blot (A) and Western blot (B) for determining the expression of p43.
+/+: wild type mouse (WT);
+/−: heterozygous mutant mouse;
−/−: homozygous mutant mouse (Ho).

In another preferred embodiment of the present invention, the nucleotide sequence of p43 allele in the p43 mutant mice is determined, and thereby it can be confirmed that the gene trap vector is inserted at the first intron of the p43 gene (See FIG. 1). The mutation of p43 is determined by Southern blot and PCR analysis (See FIG. 2) and the mutational effect on the expression of p43 is determined by Northern and Western blot (See FIG. 3). The mating of the heterozygous mutant mice generated 16 of wild type, 53 of heterozygous mutant mice and 28 of homozygous mutant mice. This ratio is close to the Mendelian segregation, indicating no significant embryonic lethality of the mutant mice. Interestingly, the homozygous mutants significantly reduced body size compared to the wild type mice (data not shown).

It has been reported that p43 is associated with immune mechanism and works on endothelial cells [Chang S. Y., et al., *J. Biol. Chem.*, 277:8388-8394, 2002; Park H-Y., et al., *J. Leukocyte Biol.* 71:223-230, 2002; Ko Y-G., et al., *J. Biol. Chem.* 276:23028-23033, 2001]. We expected that p43 might be involved in the processes of inflammation and angiogenesis occurring in the wound healing process. Thus, to confirm our expectation, the biopsies were introduced to the wild type and homozygous mutant mice, and the healing process was compared by gross examination and histological inspection. The wounds in the mutant mice (Ho) recovered at much slower rate compared to those in the wild type mice and direct administration of the purified p43 to the wound region of the wild type mice stimulated the healing process (See FIG. 4). The cross-sections of the wound showed the increase of granulation tissue and rapid re-epithelization in the wounds of the wild type mice treated with p43 (See FIG. 5).

Further, immunostaining of the wound regions with an antibody that is specific to macrophage/monocyte showed the enrichment of these cells in the wound region tissue of the p43-treated wild type mice (WT+p43) while fewer numbers of these cells were observed in the wound region tissue of the p43 mutant mice (Ho) (See FIG. 6). The macrophage/monocyte-specific antibody may include, but not limited to, anti-MOMA-2 antibody. The immunostaining of the wound regions with an antibody specific to endothelial cells showed that vascularization was also significantly enhanced in the p43-treated wild type mice (WT+p43) while the reverse was the case in the p43 mutants (Ho) (See FIG. 6). The antibody specific to endothelial cell may include, but not limited to, anti-CD31 antibody.

To determine the effect of p43 on the proliferation of different cells in the wound region, we have treated the cultivated foreskin fibroblast cells with p43. The proliferation of fibroblasts was significantly increased in dose-dependent manner by p43 (See FIG. 7). p43 did not stimulate the proliferation of keratinocyte and endothelial cells (data not shown). To see whether p43 can also show the proliferative effect on the fibroblasts in the dermal region of the wound area, we have generated the wound in the back skin of the mice and treated p43 after wounding twice a day in every other day. The proliferation of dermal fibroblasts was then compared by the immuno-fluorescence staining with anti-Ki67 antibody 3 days after wounding. The proliferation of dermal fibroblasts was stimulated in the p43 treated wound region (See FIG. 8). This result is consistent with the effect of p43 on the cultivated fibroblasts. All of these results indicate that p43 can stimulate the proliferation of fibroblasts.

To further clarify that p43 stimulates the generation of endothelial cell and induces angiogenesis, the present inventors carried out several different experiments that can determine the activity of p43 in angiogenesis.

First, the present inventors investigated whether p43 induces the migration of endothelial cells by cellular wound migration assay. In this assay, the endothelial cell migration was enhanced in the presence of p43 (See FIG. 9A). Then, the endothelial cells were cultivated on Matrigel and then the stimulated tube formation was also observed in the presence of p43 (See FIG. 9B). Secondly, chorioallantoic membrane assay (CAM) was conducted. It could be seen that blood vessels were attracted to the area to which p43 was spotted (See FIG. 9C).

Lastly, the matrigel plugs containing p43 were used to see how p43 affects neovascularization. As a positive control, the present inventors used basic fibroblast growth factor (bFGF) which was known to be associated with heparin in various forms and then to promote angiogenesis, epithelization and the deposition of collagen fiber (Tsuboi, R. et al., *J. Exp. Med.* 172:245, 1990; Kinsnorth, A. N. et al., *Br. J. Surg.* 77:409, 1990). The blood vessel formation within the gel was monitored by immunostaining with the antibody specific to endothelial cells. It could be confirmed that the gels containing bFGF or p43 showed strongly enhanced neovascularization (See FIG. 10). The result of immunostaining with the antibody specific to macrophage/monocyte was consistent with the result above (See FIG. 10). Further, it could be seen that the gels containing bFGF or p43 contained higher concentration of red blood cells than the control (See FIGS. 10 and 11).

Best Mode For Carrying Out The Invention

This invention is further illustrated by the following examples, which are not be construed in any way as imposing limitations upon the scope thereof.

EXAMPLE 1

Preparation of p43 Mutant Mouse

To prepare p43 mutant mice, p43 structural gene was allowed to be mutated using the gene trap method [Cecconi, F. & Meyer, B. I., *FEBS Lett.*, 480:63-71, 2000]. The gene trap vector, VICTR20 (Lexicon Genetics, USA) was used to mutate the genomic DNA of SvEvBrd mice (Lexicon Genetics, USA) according to Zambrowicz's method [Zambrowicz, B. P. et al., *Nature* 392:608-611, 1998]. The mutated genomic DNA was introduced into the embryonic stem cells derived from 129/SvEvBrd mice (Omnibank) to generate the mutant library. In the library, the clone containing p43 gene disrupted by the insertion of the gene trap vector was screened and called 'OST58507'. The clone was used to generate the heterozygous C57/BL6 mice (Samtako) by the standard method of Lexicon Genetics. The mating of the heterozygous mice generated 16 of wild type, 53 of heterozygous mutant mice and 28 of homozygous mutant mice. The ratio is close to the Mendelian segregation, indicating no significant embryonic lethality of the mutant.

EXAMPLE 2

Characterization of p43 Mutant Mouse 2.1 Determination of the Gene Trap Vector's Site Inserted into p43 Allele To determine the site where the gene trap vector was inserted into p43 allele, the p43 mutant allele was analyzed by sequencing. The sequencing was determined by Pangenomcis, a company for sequence analysis. As shown in FIG. 1, the first exon (Exon I) and second exon (Exon II) of p43 mutant gene were separated by the intron of about 7 kb. It was confirmed that the gene trap vector was inserted at about 1.5 kb downstream of the first exon.

2.2 Southern Blot

The genomic DNA was isolated from the tail of each mouse and digested with NcoI. The cleaved DNA fragments were separated by denaturing gel electrophoresis. Then, southern blot analysis was performed using the neomycin resistant gene (Neo$^r$) (SEQ ID NO: 2) of the gene trap vector or the HindIII fragment (SEQ ID NO: 3) of the p43 mutant gene as a prove, according to a conventional method [Southern, E. M., *J. Mol. Biol.*, 98:503, 1975]. As shown in FIG. 2A, the Neor gene of the gene trap vector and the p43 mutant gene (7 kb) were detected in the homozygous mutant mice. However, the Neo$^r$ gene was not detected in the wild type mice. In the heterozygous mutant mice, the Neo$^r$ gene was mildly detected and both intact p43 gene (10 kb) and the p43 mutant gene (7 kb) were detected. The size of the p43 mutant gene (7 kb) was smaller than that of the intact p43 gene (10 kb) because of the presence of Nco I site within Neo$^r$ gene of the gene trap vector. From the results, it can be demonstrated that the p43 mutant mouse of the present invention contains a mutation within the p43 gene.

2.3 PCR

To amplify the 1 kb DNA fragment containing the first intron of the p43 gene, the genomic DNA was used as a template for PCR analysis with IF3 primer (SEQ ID NO: 4) and IR3 primer (SEQ ID NO: 5) (See FIG. 1). To amplify the 2.2 kb DNA fragment containing a portion of the gene trap vector and a portion of the p43 gene, pKOF2 primer (SEQ ID NO: 6) and the IR3 primer were used in PCR analysis (See FIG. 1). For the PCR analysis, the template DNA was denatured at a temperature of 94° C. for 5 min and cycled 25 times at 94° C. for 1 min, at 57° C. for 1 min and at 72° C. for 1 min. As can be seen from FIG. 2B, only one band of 1 kb was detected in the wild type mice (+/+) and two bands corresponding to 1 kb and 2.2 kb, respectively, were detected in the heterozygous mutant mice (+/−). In the homozygous mutant mice (−/−), a band of 2.2 kb was only detected. From the results, it can be demonstrated that the p43 mutant mouse of the present invention contains a mutation within the p43 gene.

EXAMPLE 3

Expression of p43 by p43 Mutant Mouse 3.1 Northern Blot

For Northern analysis, total cellular RNA was prepared from mouse embryonic fibroblast (MEF) cells using RNeasy Midi Kit (QIAGEN) according to the manufacturer's instruction. The isolated RNA was separated on denaturing gel, and then transferred to the Hybond-N$^+$ membrane (Amersham). The RNAs on the membranes were hybridized with the specific probes for p43 set forth in SEQ ID NO: 7. As shown in FIG. 3A, p43 mRNA was detected in the wild type (+/+) and the heterozygous mutant mice, but was not detected in the homozygous mutant mice (−/−). It indicates that p43 is not expressed in p43 mutant mice (−/−) of the present invention.

3.2 Western Blot

For Western blot analysis, the protein was isolated from the mouse organ according to Ziak et al. (Ziak M, et al., *Biochem. Biophys. Res. Commun.* 280:363-367, 2001). Western blotting was carried out with anti-p43 antibody as described previously [Park S. G., et al., *J. Biol. Chem.* 274:16673-16676, 1999]. As shown in FIG. 3B, p43 protein was detected in the wild type (+/+) and the heterozygous mutant mice, but was not detected in the homozygous mutant mice (−/−). It was consistent with the result of the Northern blot.

EXAMPLE 4

Stimulatory Activity of p43 in Wound Healing 4.1 Gross Appearance

For gross appearance, the back skin and panniculus carnosus muscle of 7 to 8 weeks old mice (wild type and homozygous mutant mice) were excised according to Werner et al.

[Werner, S., et al., *Science* 266:819-822, 1994]. Firstly, the present inventor disinfected the back skin of mice with 70% ethanol, and shaved fur from the back under avertin anesthetization. Then, the circular excision wound of bilateral symmetry having a diameter of 0.5 cm was prepared using a circular punch of 1 cm on the back skin. The wounds were left uncovered without the drug treatment or dressing. Meanwhile, p43 was prepared from *E. coli* as described previously [Park S. G., et al., *J. Biol. Chem.* 274:16673-16676, 1999]. 4 μg of the purified p43 was dissolved in 5 μl of PBS buffer containing 20% glycerol. Each group of the wounds in 25 wild type mice was treated with either p43 (4 μg/wound) or the PBS buffer with 20% glycerol alone (control), 4 times at 2 days interval. Also, the p43 mutant mice were left without the treatment of p43. The wound closure was monitored daily using the Image-Pro Plus Software (Media Cybernetics).

Figure 4A:
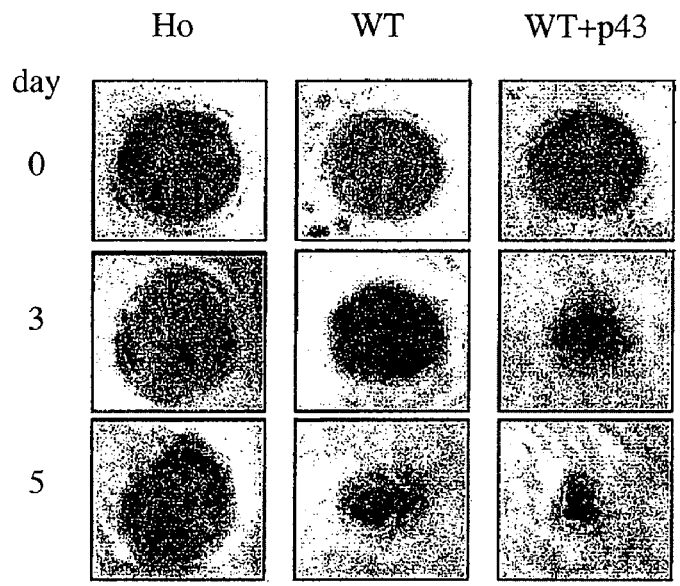
FIG. 4 is a photograph showing wound healing levels with the lapse of time (A) and a bar graph representing a percentage of wound healing levels to an initial wound area (B).
Figure 4B:
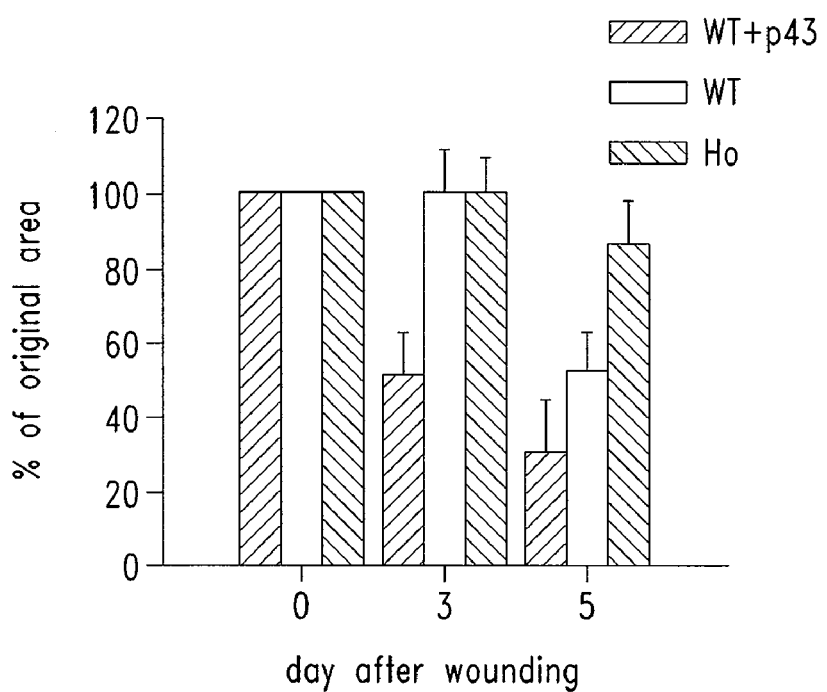

As shown in FIG. 4A, the wounds in the wild type mice treated with p43 (WT+p43) recovered at much faster rate compared to those in the homozygous mutant mice (Ho) or the wild type mice which were not treated with p43 with the lapse of time. However, the wounds in the homozygous mutant mice (Ho) recovered at a much slower rate compared to those in the wild type mice which were not treated with p43 even after much time had passed. The wound closure was calculated as the percentage of the initial wound area. As shown in FIG. 4B, the wound area of the wild type mice treated with p43 (WT+p43) was significantly decreased with the lapse of time.

4.2 Histochemical Analysis 5 day-aged wounds were isolated with 3 mm of adjacent normal tissue, fixed overnight in Bouin's solution (Sigma, HT10-1-32), and then embedded in paraffin. Paraformaldehyde-fixed paraffin sections (6 μm) of the wounds were stained by the Masson Trichome procedure (Lund, L. R., et al., *EMBO J.* 18:4645-4656, 1999). Only littermates of the same sex were used for direct histological comparison.

As shown in FIG. 5, the wild mice treated with p43 (WT+p43) were confirmed to indicate the increase of granulation tissue (purple sites below the wound areas) and rapid re-epithelialization by the increase of advancing epithelial layer (arrows). However, the homozygous mutant mice (Ho) showed little increase of advancing epithelial layer in the wounds.

4.3 Induction of Macrophage/Monocyte and Endothelial Cells by p43

5 day-aged wounds were isolated with 3 mm of adjacent normal tissue. The isolated wounds were fixed in 4% paraformaldehyde in PBS and then frozen in the OCT compound (Sakura). The cyro-sections of the wounds were analyzed by immune-fluorescence. To detect macrophage/monocyte and endothelial cells, the frozen sections were incubated in 1.7 μg/ml of anti-mouse MOMA-2 antibody (Serotec) and 1.0 μg/ml of anti-CD31 antibody (Pharmingen) that are specific to the cells, respectively. After incubation for 1 hour with the primary antibodies, 1.0 μg/ml of FITC-conjugated secondary antibody was added and further incubated for 1 hour. The wounds were then counterstained with propidium iodide (1 μg/ml), mounted on slides and investigated using confocal immunofluorescence microscopy (μRadience; BioRad).

As shown in FIG. 6, the wound tissues of the wild type mice treated with p43 (WT+p43) showed the enrichment of the macrophage/monocyte while the wound tissues of the homozygous mutant mice (Ho) showed fewer numbers of the macrophage/monocyte. Also, the immunostaining of the wounds with the antibody specific to endothelial cells showed that vascularization was also significantly enhanced in the p43-treated wounds while the reverse was the case in the p43 mutants (See FIG. 6).

4.4 Effect of p43 on the Proliferation of Fibroblasts 4.4.1 Effect of p43 on the Cultivated Fibroblasts To determine the effect of p43 on the proliferation of foreskin fibroblasts, the foreskin fibroblasts(American Type Culture Collection) were cultivated in the presence of the different amounts of p43 (1, 10, and 100 ng/ml) for 48 h, and then in fresh medium containing 1 uCi tritium-labeled thymidine for 4 h. After washing and lysing the cells with RIPA buffer, the amounts of the incorporated thymidine were quantified by liquid scintillation counting.

As shown in FIG. 7, the proliferation of fibroblasts was significantly increased in dose-dependent manner by p43.

4.4.2 Histological Analysis

To determine the effect of p43 on the proliferation of dermal fibroblasts in the cutaneous wound area, the cutaneous wounds were generated on the back skin of 7 to 8 weeks old mice mice according to Werner et al. [Werner, S., et al., *Science* 266:819-822, 1994]. Meanwhile, p43 was prepared from *E. coli* as described previously [Park S. G., et al., *J. Biol. Chem.* 274:16673-16676, 1999]. 4 μg of the purified p43 was dissolved in 5 μl of PBS buffer containing 20% glycerol. The wounds in 25 wild type mice were treated with either p43 (4 ug/wound) or the PBS buffer with 20% glycerol alone (control), twice in every other days. The mice were sacrificed in 3 days after wounding and the wound area was isolated for histological analysis. The crosssection of the wound area was stained using hematoxylin and eosin. The boxed region in the wound (see FIG. 8 Left) was analyzed by immuno-fluorescence with the antibody against Ki-67 that is the marker of the cell proliferation (Ben-Izhak, O. et al. Ki-67 antigen and PCNA proliferation markers preducts survival in anorectal malignant melanoma. Histopathology 41, 519-525, 2002). 3 day-aged wounds were isolated with 3 mm of adjacent normal tissue. The isolated wounds were fixed in 4% paraformaldehyde in PBS and frozen in OCT compound. The frozen sections (6 μm) were equilibrated 3 times with PBS for 5 min. Non-specific interactions were blocked with PBS containing 0.1% Tween 20, 1% non fat milk for 2 h at room temperature and sections were incubated with 1/50 diluted anti-KI67 antibody (Santacruz) in PBST (PBS containing 0.1% Tween 20) for 2 hrs at 37° C. The sections were washed 2 times with PBST and subsequently incubated for 1 h at 37° C. with the FITC conjugated antibody. The sections were counsterstained with propium iodide (10 ug/ml) for 15 min and washed 3 times with PBST for 5 min. Fluorescence signals were examined under the confocal immunofluorescence microscopy (Radiance, BioRad).

As shown in FIG. 8, p43 can stimulated the proliferation of fibroblasts.

EXAMPLE 5

Effect of p43 on Angiogenesis 5.1 Cellular Wound Migration Assay

To investigate whether p43 induces the migration of endothelial cells, the cellular wound migration assay was performed. First, aorta was excised from the butchered cattle and washed by dipping in cold PBS buffer containing 1% penicillin and 0.25 μg/ml fungizone. Then, bovine aortic endothelial cells (BAECs) were isolated from the surface of the tracheal aorta using a razor blade and incubated in DMEM containing 20% fetal bovine serum (FBS). The incubated cell cultures were wounded with a razor blade in 2 mm in width and the injury lines were marked. Then, the cultures were washed with serum-free medium and further incubated in DMEM with 1% serum, 1 mM thymidine and 1 nM p43. The cells were allowed to migrate for 16 hours and then rinsed. A control was not treated with p43. The cultures were fixed with absolute methanol (100%) and stained with Giemsa (Chameleon Chemical).

As shown in FIG. 9A, the endothelial cell migration was enhanced in the presence of p43. From the result, it was demonstrated that p43 stimulates the endothelial cell migration.

5.2 Blood Tube Formation

From the result of Example 5.1 described above, it was confirmed that p43 induced the endothelial cell migration. And then, to investigate whether p43 induces blood tube formation, BAECs ($5 \times 10^5$ cells) were cultivated on Matrigel (Becton Dickinson) in the presence of 1 nM of p43 at 37° C. for 6 hours. A control was not treated with p43. Then, the changes of cell morphology were captured by phase contrast microscopy.

As shown in FIG. 9B, the stimulated tube formation was observed in the presence of p43, but in the control. The result indicated that p43 stimulates tube formation and it was consistent with the endothelial cell migration.

5.3 Chorioallantoic Membrane Assay

Fertilized chick eggs were incubated in the humidified egg breeder at 37° C. On the third day of incubation, about 2 ml of egg albumin was removed by an 18-gauge hypodermic needle to detach the developing chorioallantoic membrane (CAM) from the shell. After the incubation for additional 6 days, thermanox coverslips (Nunc) loaded with 0.1 μg of p43 (dissolved in PBS buffer containing 20% glycerol) were placed on the CAM surface and vascularization was observed. A control was not treated with p43. As shown in FIG. 9C, blood vessels were attracted to the area to which p43 was spotted.

5.4 Matrigel Plug Assay

To see how p43 affects neovascularization, matrigel plugs containing p43 were subcutaneously injected into the skin of mice and stained by Masson Trichome method, and then red blood cells within the gels were counted. First, the Matrigel (0.25 ml, Becton Dickinson) was supplemented with p43 (1 ng/ml) plus heparin (9U/ml, Sigma). PBS buffer containing 20% glycerol was used as a negative control. And as a positive control, 143 ng/ml of bFGF (R&D systems) plus heparin was used, in which bFGF was known as a growth factor to stimulate the blood tube formation by associating with heparin in a various form. The mixtures were subcutaneously injected into 7 weeks old C57BL6/J mice (Samtako) in a dose of 0.25 ml/site. The mice were sacrificed 7 days after the inoculation and the gets were removed, fixed in 4% paraformaldehyde for 24 hours. The gel plugs were embedded in the OCT compound (Sakura) and then sliced into sections of 10 μm thick using Cyo-microtome (Zeiss). The sections were reacted with anti-CD31 antibodies (Pharmingen) and anti-MOMA2 antibodies (Serotec) that are specific to the endothelial cells and macrophage/monocyte, respectively, and then stained by Masson Trichome method [Lund, L. R., et al., *EMBO J.* 18:4645-4656, 1999]. As a result, in the presence of p43, neovascularization was strongly enhanced (See FIG. 10, top row) and macrophage/monocyte were also recruited to the gel compared to the control (See FIG. 10, middle row, green fluorescence). Interestingly, other cells were also enriched in the gels treated with p43 (red fluorescence).

The blood vessel formation within the gels was also monitored by counting red blood cells. As shown in FIG. 10 (bottom row, arrowheads), the gels containing bFGF or p43 contained higher concentration of red blood cells than the control. Further, the concentration of hemoglobin within the gels was determined as described previously [Passaniti, A., et al., *Lab. Invest.*, 67:519-528, 1992]. As shown in FIG. 11, the gels containing bFGF or p43 contained higher concentration of hemoglobin than the control.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The entire disclosure of Korea Patent Application No. 2002-42858, filed on Jul. 22, 2002 including its specification, claims, drawings and summary are incorporated herein by reference in its entirety.

What is claimed is:

1. A method for stimulating wound healing in a subject in need thereof, comprising: administering to a wound of the subject an effective amount of a composition for stimulating wound healing, wherein the composition comprises a polypeptide selected from the group consisting of: (a) a polypeptide having the amino acid sequence set forth in SEQ ID NO: 1; and (b) a polypeptide having at least 80% sequence homology with the polypeptide of (a).

2. The method according to claim 1, wherein the composition further comprises at least one selected from the group consisting of antibiotics, antihistamines, anti-inflammatory drugs, anti-viral drugs, anti-fungal drugs and growth factors.

3. The method according to claim 1, wherein the composition further comprises a pharmaceutically acceptable carrier.

4. The method according to claim 1, wherein the composition is formulated with any one form selected from the group consisting of a powder, liniment, gel, lotion, cream, ointment, paste, puff, aerosol and suppository.

5. The method of claim 1, wherein said wound is selected from the group consisting of burn, ulcer, trauma, post-surgical, post-childbirth, chronic wound and dermatitis.

6. The method of claim 5, wherein said burn is selected from the group consisting of sunburn, chemical burn, radiation burn and thermal burn.

7. The method of claim 5, wherein said ulcer is selected from the group consisting of pressure ulcer, plaster ulcer and decubitus ulcer.

8. The method for claim 5, wherein said chronic wound is selected from the group consisting of bedsores, pressure sores, diabetes-related and poor circulation-related.

9. The method of claim 5, wherein said dermatitis is selected from the group of consisting of impetigo, intertrigo, folliculitis and eczema.

10. The method of claim 1, wherein the polypeptide consists of the amino acid sequence set forth in SEQ ID NO:1, or consists of an amino acid sequence having at least 90% sequence identity to the polypeptide of (a).

* * * * *